US011312678B2

(12) United States Patent
Keyes et al.

(10) Patent No.: US 11,312,678 B2
(45) Date of Patent: Apr. 26, 2022

(54) SOLID-LIQUID SEPARATION PROCESSES USING A LARGE PORE FILTER

(71) Applicant: Ineos US Chemicals Company, Naperville, IL (US)

(72) Inventors: Timothy H. Keyes, Naperville, IL (US); Anders Bitsch-Larsen, Naperville, IL (US)

(73) Assignee: Ineos US Chemicals Company, Naperville, IL (US)

( * ) Notice: Subject to any disclaimer, the term of this patent is extended or adjusted under 35 U.S.C. 154(b) by 0 days.

(21) Appl. No.: 17/255,157

(22) PCT Filed: Jun. 28, 2019

(86) PCT No.: PCT/US2019/039880
§ 371 (c)(1),
(2) Date: Dec. 22, 2020

(87) PCT Pub. No.: WO2020/006446
PCT Pub. Date: Jan. 2, 2020

(65) Prior Publication Data
US 2021/0246096 A1 Aug. 12, 2021

Related U.S. Application Data (60) Provisional application No. 62/691,798, filed on Jun. 29, 2018.

(51) Int. Cl.
| | |
|---|---|
| *C07C 51/47* | (2006.01) |
| *B01D 33/09* | (2006.01) |
| *B01D 33/60* | (2006.01) |
| *B01D 33/62* | (2006.01) |
| *B01J 31/04* | (2006.01) |
| *C07C 51/487* | (2006.01) |

(52) U.S. Cl.
CPC ............... *C07C 51/47* (2013.01); *B01D 33/09* (2013.01); *B01D 33/60* (2013.01); *B01D 33/62* (2013.01); *B01J 31/04* (2013.01); *C07C 51/487* (2013.01); *B01D 2201/184* (2013.01); *B01J 2231/643* (2013.01)

(58) Field of Classification Search
CPC ......... C07C 63/26; C07C 51/43; C07C 51/47; C07C 51/487; B01D 2201/184; B01D 2201/347; B01D 33/09; B01D 33/60; B01D 33/62; B01D 33/801; B01J 2231/643; B01J 31/04
See application file for complete search history.

(56) References Cited

U.S. PATENT DOCUMENTS

| | | | | |
|---|---|---|---|---|
| 4,179,268 A | * | 12/1979 | Reinwald | ............... C11D 3/128 8/137 |
| 5,200,557 A | | 4/1993 | Gee et al. | |
| 5,292,934 A | * | 3/1994 | Sikkenga | ............... C07C 51/255 562/413 |
| 5,583,254 A | * | 12/1996 | Turner | .................... C07C 51/43 562/414 |

FOREIGN PATENT DOCUMENTS

| | | |
|---|---|---|
| JP | H09-295957 A | 11/1997 |
| WO | 2010/119484 A1 | 10/2010 |
| WO | 2016/025399 A1 | 2/2016 |
| WO | WO-2016025399 A1 * | 2/2016 ............. B01D 33/09 |

\* cited by examiner

*Primary Examiner* — Yevgeny Valenrod
*Assistant Examiner* — Blaine G Doletski
(74) *Attorney, Agent, or Firm* — McDonnell, Boehnen, Hulbert & Berghoff LLP (57) ABSTRACT

Solid/liquid separation processes using a large pore filter. One aspect of the disclosure is a process comprising filtering a solid/liquid mixture of a collection of solid aromatic carboxylic acid particles in a solvent in a first zone of a rotary pressure filter apparatus to form a filter cake on a filter surface, and removing the filter cake from the filter surface.

17 Claims, 4 Drawing Sheets

SOLID-LIQUID SEPARATION PROCESSES USING A LARGE PORE FILTER

CROSS-REFERENCE TO RELATED APPLICATIONS

This application is a U.S. National Phase Application under 35 U.S.C. § 371 of International Application No. PCT/US2019/039880, filed Jun. 28, 2019, which claims the benefit of priority of U.S. Provisional Patent Application No. 62/691,798, filed Jun. 29, 2018, which are hereby incorporated by reference in their entirety.

BACKGROUND OF THE DISCLOSURE

Field of the Disclosure

The present disclosure relates generally to solid/liquid separation processes.

Technical Background

In processes in the chemical, food, and pharmaceutical industries, various separation techniques are used to isolate one material from another. Common techniques for separating solid materials from a liquid include vacuum or pressure filtration, drying, centrifugation, sedimentation and clarification. When a very pure solid product is required, separation may occur in multiple stages and may be combined with washing steps. For example, a solid recovered from one of the techniques noted above may be washed or reslurried with aciditional liquids in order to remove impurities before being subjected to another solid/liquid separation technique to recover a final, more pure product.

Multiple-stage separation techniques may result in higher purities of solid products, but may require substantially more investment in equipment. One highly successful method to reduce capital expenditures in a multi-stage separation is through the use of a rotary pressure filter apparatus. Rotary pressure filter apparatuses have been designed to perform more than one of the steps of a multiple-stage separation technique in a single piece of equipment by progressing the material being processed through separate work zones. For example, known rotary pressure filter apparatuses perform a filtration in a filter or feed zone to form a filter cake, followed by a washing of the filter cake in one or more wash zones. The washed filter cake may be dried in a drying zone before leaving the rotary pressure filter. Rotary pressure filter apparatus are generally known in the art and are disclosed, for example, in U.S. Pat. Nos. 2,741,369, 7,807,060, and U.S. Patent Application Publication No. 2005/0051473.

There remains a need to improve separation processes which utilize rotary pressure filter apparatus.

SUMMARY OF THE DISCLOSURE

The scope of the present disclosure is not affected to any degree by the statements within the summary.

According to one aspect of the disclosure, a process for recovering a solid aromatic carboxylic acid from a solid/liquid mixture of the solid aromatic carboxylic acid in a solvent is disclosed. The solid aromatic carboxylic acid is in the form of a collection of particles having a distribution of particle sizes having a median particle size. The method include filtering the solid/liquid mixture to form a filter cake on a filter surface, the filter cake comprising the solid aromatic carboxylic acid; and removing the filter cake from the filter surface; and wherein the average pore size of the filter surface is greater than the median particle size of the collection of particles.

Other aspects of the disclosure will be apparent to those skilled in the art in view of the description that follows.

DETAILED DESCRIPTION

In various aspects, the processes of the disclosure provide an efficient manner of recovering components of the filtrate of a solid/liquid mixture filtration.

Additional features of the processes of the disclosure will now be described in reference to the drawing figures.

The present inventors have noted that solid/liquid mixture filtration performance is advantageously improved when a filter with a relatively large pore size is used. Specifically in the context of separation of solid aromatic carboxylic acid particles from a solvent (e.g., a solvent that is substantially water, or a monocarboxylic acid solvent), the present inventors have noted increased flow rate (e.g., of the monocarboxylic acid solvent, or of a wash fluid) and resistance to fouling when the average pore size of the filter is larger than the mass mean diameter of the particles.

Accordingly, one aspect of the disclosure provides a process including filtering a solid/liquid mixture of a collection of solid aromatic carboxylic acid particles in a solvent (e.g., from a crystallization zone or a purification zone) in a first zone of a rotary pressure filter to form a filter cake on a filter surface, the collection of particles having a median particle size of less than the average pore size of the filter surface. In certain embodiments, the filter cake is washed with an aqueous wash fluid in a second zone of the rotary pressure filter to form a wet filter cake, which is then removed from the filter surface.

Moreover, the present inventors have further noted that evaporation (e.g., flash evaporation) of solvent in liquid entrained in a filter causes deposition of the solute of that liquid in the filter (i.e., fouling), which can decrease filter performance. Specifically in the context of a wet filter cake comprising solid aromatic carboxylic acid (e.g., formed by filtering a solid/liquid mixture of solid aromatic carboxylic acid in a monocarboxylic acid solvent), the present inventors have noted that removing the wet filter cake from the filter surface without substantially drying the filter cake can decrease or even prevent deposition of one or more solutes of the monocarboxylic acid solvent in the filter. Accordingly, in certain embodiments of the processes as otherwise described herein, the wet filter cake is removed from the filter surface without substantially drying the wet filter cake.

Figure 1:
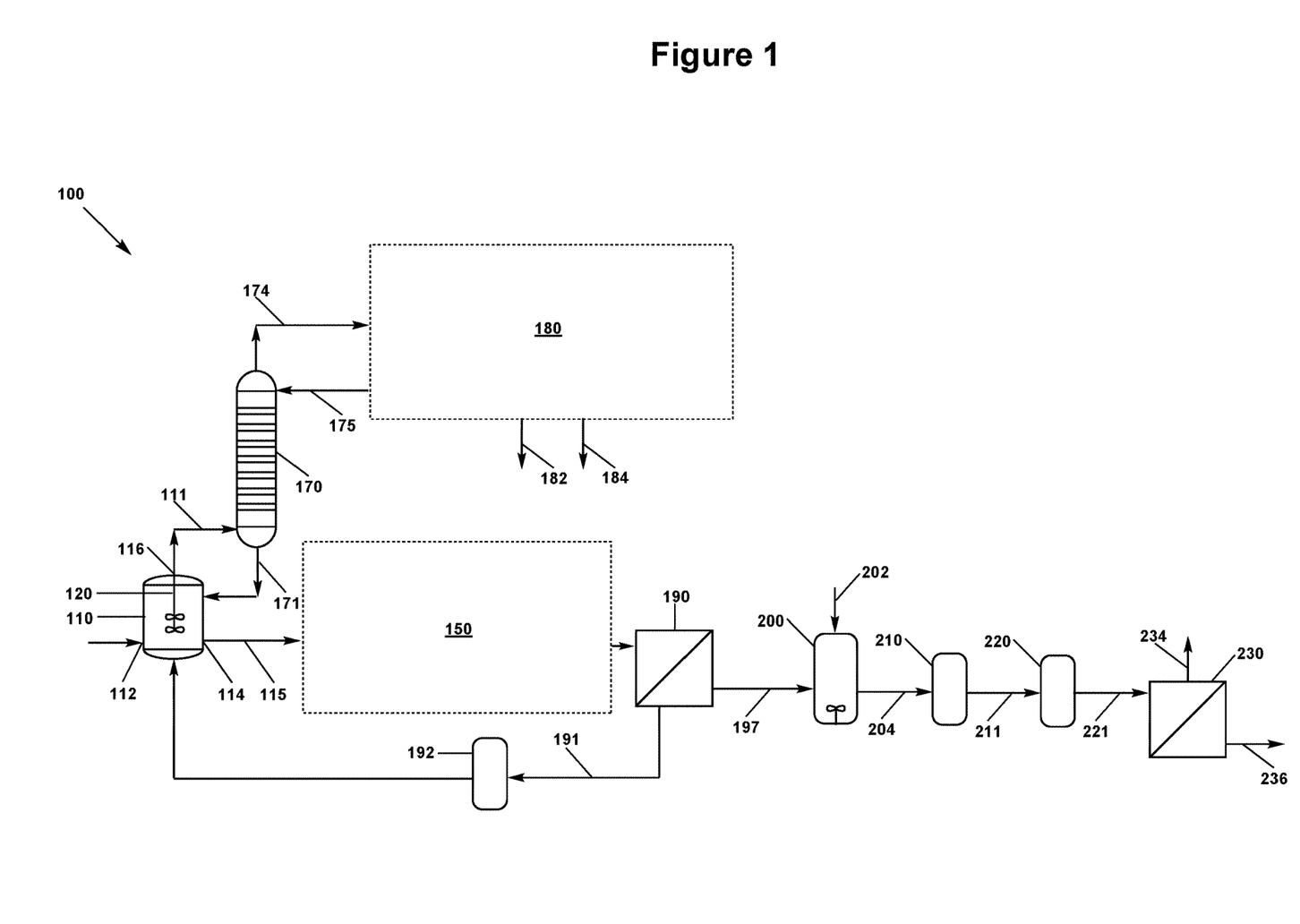
FIG. 1 is a process flow diagram for the manufacture and recovery of purified forms of aromatic carboxylic acids in accordance with one embodiment of the present disclosure.

FIG. 1 is a process flow diagram for manufacturing and recovering aromatic carboxylic acids in accordance with one embodiment of the present disclosure. FIG. 1 depicts a number of aciditional elements for use in processes according to certain embodiments of the disclosure. A system for performing a process 100 of FIG. 1 includes a reaction zone that includes an oxidation reactor 110 configured for liquid-phase oxidation of feedstock to provide a reaction zone effluent; a crystallization zone 150 configured for forming solid crude aromatic carboxylic acid from the reaction zone effluent, and comprising one or more crystallizers in series; a solid/liquid separation device 190 configured for separating solid crude aromatic carboxylic acid (and oxidation by-products) from liquid; a mixing zone including a purification reaction mixture make-up vessel 200 configured for preparing mixtures of crude aromatic carboxylic acid in purification reaction solvent; a purification zone including a hydrogenation reactor 210 configured for contacting the crude aromatic carboxylic acid with hydrogen in the presence of a catalyst to form a purified aromatic carboxylic acid; a recovery zone comprising a crystallization zone 220 including at least one crystallizer configured for forming a slurry stream comprising solid purified aromatic carboxylic acid and a vapor stream, wherein the vapor stream comprises steam and hydrogen; and a solid/liquid separation device 230 configured for separating solid purified aromatic carboxylic acid from liquid.

However, the person of ordinary skill in the art will appreciate that the integration of processes in FIG. 1 is meant to be purely representative, and various other integrated and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams of compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

As described above, the feedstock includes a substituted aromatic hydrocarbon. Representative feedstock materials suitable for use in the processes of the disclosure include but are not limited to aromatic hydrocarbons substituted at one or more positions with at least one substituent that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone; 1,2,4-trimethylbenzene; 1-formyl-2,4-dimethyl-benzene; 1,2,4,5-tetramethylbenzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present disclosure are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) of aromatic rings that, in some embodiments, are fused (e.g., naphthalene, anthracene, etc.) and, in other embodiments, are not. In some embodiments, the aromatic carboxylic acid comprises only one carboxylic acid (e.g., $-CO_2H$) moiety or a salt thereof (e.g., $-CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be performed in the oxidation zone (e.g., oxidation reactor 110) is a liquid phase oxidation that comprises contacting oxygen gas and a feed material comprising an aromatic hydrocarbon having one or more substituents oxidizable to carboxylic acid groups in a liquid phase reaction mixture. In some embodiments, the liquid phase reaction mixture comprises a monocarboxylic acid solvent and water in the presence of an oxidation catalyst comprising at least one heavy metal component (e.g., Co, Mn, V, Mo, Cr, Fe, Ni, Zi, Ce, Hf, or the like, and combinations thereof) and a promoter (e.g., halogen compounds, etc.). In certain desirable embodiments, the monocarboxylic acid solvent includes acetic acid (e.g., is at least 90% acetic acid, or at least 95% acetic acid).

In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in the reaction zone, e.g., in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air, as a source of oxygen, may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reaction zone, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized monocarboxylic acid, water vapor, gaseous by-products from the oxidation reaction, carbon oxides, nitrogen from the air charged to the reaction, unreacted oxygen, and the like, and combinations thereof.

The gaseous stream may be removed from the reactor through vent 116 and sent in a stream 111 to a distillation column 170. The distillation column 170 is configured to separate water from the solvent monocarboxylic acid and return a monocarboxylic acid-rich liquid phase to the reactor in stream 171. A water-rich gaseous stream is removed from the distillation column 170 in stream 174 and sent for further processing to an off-gas treatment zone 180. Reflux is returned to the distillation column 170 in stream 175. The reflux liquid may include a condensed, liquid phase component 182 of the water-rich gaseous stream 174, or may include fluid from other sources, such as liquid stream 193 or 234.

The person of ordinary skill in the art will appreciate that the off-gas treatment zone can include a variety of components, for example, one or more of a condenser a disengagement drum configured to separate the effluent of the condenser into a gas-phase component and a liquid-phase component; a scrubber configured to remove impurities (e.g., alkyl aromatic hydrocarbons, solvent monocarboxylic acid) from the gas-phase component; a catalytic oxidation ("catox") unit configured to remove impurities (e.g., organic components, CO) from the gas-phase component; a bromine scrubber, configured to remove bromine from the gas-phase effluent of the catox unit; and an expander and a turbine, configured to convert energy from the gas-phase component to electricity. The components of the off-gas treatment zone may be arranged in a number of configurations. For example, the gas-phase effluent of the bromine scrubber may be sent to the expander and turbine. In another example, the gas-phase effluent of the absorber may be sent to the expander and turbine. In yet another example, the gas-phase effluent of the disengagement drum may be sent to the expander and turbine. A liquid-phase component 182 is removed from the off-gas treatment zone 180, and may include the liquid-phase effluent of the disengagement drum or the scrubber. A gas-phase component 184 is removed from the off-gas treatment zone 180, and may include the gas-phase effluent of the disengagement drum, the absorber, the bromine scrubber, or the expander and turbine.

The person of ordinary skill in the art will appreciate that the off-gas treatment zone can be configured in a variety of manners. Examples of processing and treatment of the reaction off-gas stream, and sources of reflux fluids are more fully described in U.S. Pat. Nos. 5,723,656, 6,137,001, 7,935,844, 7,935,845, and 8,173,834.

In some embodiments, solid crude product may be recovered from the reaction zone effluent by crystallization in one or more stages, such as in a crystallization zone 150, as shown in FIG. 1. In the embodiment shown in FIG. 1, liquid-phase reaction mixture is removed from reaction vessel 110 through slurry outlet 114 and directed in stream 115 to one or more in-series crystallizers of crystallization zone 150, to form solid oxidation product. Cooling in the crystallizers may be accomplished by pressure release. One or more of the crystallizers may be vented to remove vapor resulting from pressure let down and generation of steam from the flashed vapor to a heat exchanger (not shown).

In certain embodiments of the processes as otherwise described herein, the aromatic carboxylic acid prepared by the process comprises terephthalic acid, and the substituted aromatic hydrocarbon of the feedstock comprises para-xylene. For example, in certain such embodiments, the substituted aromatic hydrocarbon of the feedstock is at least 99% by weight para-xylene, and/or the aromatic carboxylic acid prepared by the process is at least 95% by weight terephthalic acid.

A variety of process operations can be used in recovery of the crystallized carboxylic acid. In certain embodiments as otherwise described herein, at least a portion of an effluent of a last crystallizer of the crystallization zone is separated to form an aromatic carboxylic acid-rich stream and a solvent-rich stream. For example, in the process depicted in FIG. 1, the crystallization zone 150 is in fluid communication with a solid/liquid separation device 190. The solid/liquid separation device 190 is configured to receive a slurry of solid product from the crystallization zone 150, and is further configured to separate the slurry of solid product to form an aromatic carboxylic acid-rich stream 197 and one or more solvent-rich streams (in FIG. 1, 191) for transfer to mother liquor drum 192. A portion of the mother liquor and, in some embodiments, a major portion of the mother liquor, may be transferred from drum 192 to the reaction zone (e.g., to oxidation reactor 110). In such a way, monocarboxylic acid solvent, water, catalyst, and/or oxidation reaction byproducts dissolved and/or present as fine solid particles in the mother liquor may be returned to the liquid phase oxidation reaction.

Notably, the separation methods described herein can advantageously be used in the separation of at least a portion of a solid/liquid mixture transferred from a crystallization zone to form an aromatic carboxylic acid rich stream and one or more solvent-rich streams. Accordingly, solid/liquid separation device 190 and/or 230 can be a rotary pressure filter. Suitable rotary pressure filters are sold by BHS-Sonthofen and are disclosed for example, in U.S. Pat. Nos. 2,741,369, 7,807,060, U.S. Pat. App. 20050051473, US Pat. App. 20150182890, and WO 2016/014830.

Figure 2:
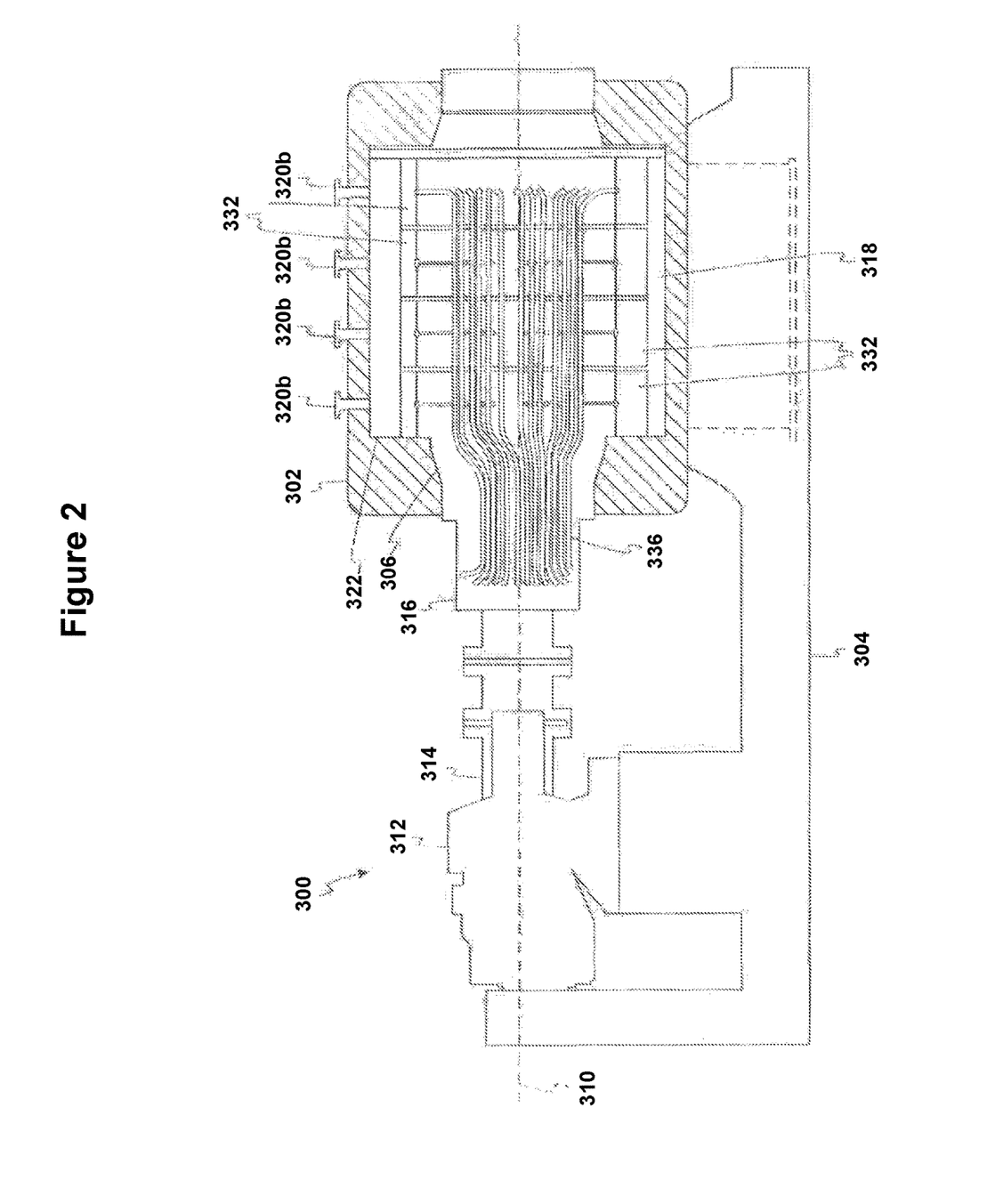
FIG. 2 shows a side view cross-section of a rotary pressure filter in accordance with one embodiment of the present disclosure.
Figure 3:
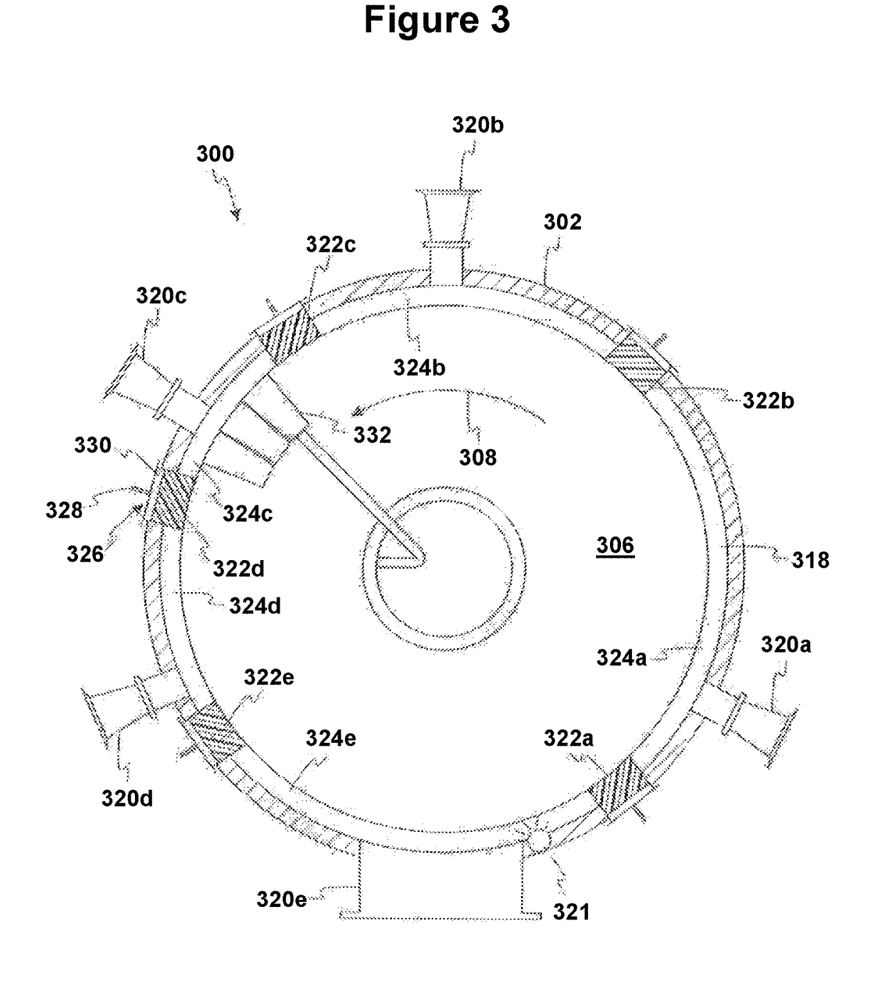
FIG. 3 shows a front view cross-section of a rotary pressure filter shown in FIG. 2.

FIG. 2 is a longitudinal cross section of a rotary pressure filter apparatus in accordance with one embodiment of the present disclosure. FIG. 3 shows a front view cross-section of the rotary pressure filter shown in FIG. 2. As shown in FIG. 2, the rotary pressure filter apparatus 300 operates under a positive pressure to filter and remove liquid from a solid/liquid mixture and to collect a solid product as a final product or as an intermediate for further processing. The rotary pressure filter apparatus 300 includes a stationary housing 302 capable of withstanding an internal pressure above ambient. The housing 302 is mounted upon a frame 304. Inside the housing 302 is a rotary filter drum 306. As shown in FIG. 3, the rotary filter drum 306 rotates as indicated by arrow 308 around an axis 310 (FIG. 2) at a speed of around 0.4 to 2 RPM, and in some embodiments at a speed of about 0.8 to 1.5 RPM. The axis 310 defines a longitudinal direction of the rotary drum 306 and the rotary pressure filter apparatus 300. The rotary filter drum 306 is driven by a drive mechanism 312, which is also mounted on the frame 304. A shaft 314 connects the drive mechanism 312 to a control head portion 316 of the rotary drum 306.

The surface of the rotary drum 306 is spaced from the inside of the housing 302 such that generally annular plenum 318 is formed therebetween. Material passageways 320*a*, 320*b*, 320*c*, 320*d*, and 320*e*, such as inlets and outlet piping, are adapted to allow passage of material between the annular plenum 318 and a location outside the housing 302.

One or more sealing members 322*a*, 322*b*, 322*c*, 322*d*, 322*e* are configured to contact the rotary drum 306 and divide the annular plenum 318 into a plurality of zones 324*a*, 324*b*, 324*c*, 324*d*, 324*e*. The sealing members 322 generally contact the rotary drum with enough pressure to pressure seal the zones 324 from each other but still allowing the rotary drum 306 to rotate. The sealing members 322 are each part of a sealing device 326 which includes an actuating mechanism adapted to members 322 in the radial direction to exert force against the rotary drum 306. In the embodiment shown, the actuating mechanism is a pneumatic device including an inlet 328 for introducing gas into a plenum 330 to exert a pressure force against the outer surface of the respective sealing member 322. Suitable pressure forces exerted by the pneumatic device include those about 0.8 to 2.0 bar above the highest pressure in any of the zones 324*a*, 324*b*, 324*c*, 324*e* of the rotary pressure filter apparatus 300. Those skilled in the art will recognize that other actuating mechanisms may be substituted for the pneumatic device.

A plurality of compartments 332 are arranged around the outer surface or circumference of the rotary filter drum 306 and rotate with the filter drum 306. The compartments 332 each include a filter member 334 (shown in one compartment in FIG. 4) adjacent the filter drum. In some embodiments the filter member comprises a filter sheet supported in a filter housing (not shown), for example, by being positioned over a support screen. In some embodiments, the filter sheet is manufactured from a polyether ketone (PEEK) polymer or a polyvinylidene difluoride (PVDF) polymer. The filter sheet can be, for example, formed as a fabric or cloth. But in other embodiments, other materials can be used, e.g., metal screen, fabric or cloth, or a glass or ceramic screen, fabric or cloth.

The present inventors have noted that it can be especially desirable to use the methods described herein in conjunction with a filter member having a relatively large pore size. Particularly, relatively large pore sizes can be desirable from the standpoint of improved flow and resistance to fouling. Accordingly, in certain embodiments as otherwise described herein, the solid carboxylic acid of the solid/liquid mixture is in the form of a collection of particles having a distribution of particle sizes having a median particle size, and the filter member has an average pore size that is greater than the median particle size of the collection of particles. For example, in certain embodiments, the median particle size of the collection of particles is less than 95%, or less than 90%, or less than 85%, or less than 80% of the average pore size of the size of the filter member. Of course, a pore size that is too large may allow too much particulate matter through; accordingly, in certain embodiments, the median particle size of the collection of particles is at least 50%, or at least 60% of the average pore size of the filter member. In certain such embodiments, the median particle size of the collection of particles is within the range of 80 µm to 200 µm, or about 90 µm to about 190 µm, or about 100 µm to about 180 µm.

Each compartment 332 also has associated with it a corresponding outlet pipe 336 which also rotates with the filter drum 306 and the compartments 332. The outlet pipes 336 are configured such that filtrate received from each compartment 332 passes through its corresponding filter member 334 adjacent the filter drum 306 and into its corresponding outlet pipe 336. The outlet pipes 336 remove the filtrate from the compartments 332 and deliver the filtrate to the control head 316, where it is collected through aciditional piping (not shown) and removed from the rotary pressure filter apparatus 300.

The compartments 332 rotate with the rotary drum 306 and accordingly pass sequentially through each of the zones 324*a*, 324*b*, 324*c*, 324*d*, 324*e*. In the embodiment shown, the compartments 332 are arranged in rows of four along the longitudinal direction 310. Those skilled in the art will recognize that other configurations of the compartments would be suitable as well.

In operation, a pressurized feed containing a solid/liquid mixture is introduced into the feed inlet material passageway 320*a* and into plenum 318 in a first zone designated as feed zone 324*a*. The solid/liquid mixture is distributed into compartment 332. In some embodiments, the pressure in the feed zone is maintained at about 3 bar(g) to about 7 bar(g), and in some embodiments, 5 bar(g) to 6 bar(g). As a result of the pressure differential that is maintained between the compartments 332 and the outlet pipes 336 and across the filter member 334 in zone 324*a*, liquid and a portion of the solid components of the solid/liquid mixture is forced through the filter member 334 into outlet pipes 336. Filtrate thus exits the rotary pressure apparatus 300 through outlet pipes 336. A portion of the solid components of the solid/liquid mixture remains on the filter members 334 in the form of a filter cake.

As the rotary drum 306 continues into the next zone 324*b*, designated as a wash zone, wash fluid is introduced into plenum 318 for distribution into the compartments 332 to wash the cake remaining on the filter members 334. In some embodiments, wash fluid is introduced at a rate of about 0.5 kg to about 1.5 kg of wash fluid per 1 kg of filter cake. The wash fluid is removed by outlet 336. In the embodiment shown, the rotary drum then continues to a second wash zone 324*c* and then to a third wash zone 324*d*, where aciditional wash fluid is introduced into zone 324*c* and 324*d*, designated as a second wash zone and a third wash zone, respectively, and the cake on the filter members 334 is again washed. As in zone 324*a*, a pressure differential is maintained between the compartments 332 and the outlet pipes 336 in zones 324b, 324c, 324d.

The wash fluid is selected to remove impurities from the filter cake while not interfering with further processing of the filter cake to recover the final solid product. In one embodiment, the wash fluid comprises water. In another embodiment, the wash fluid comprises condensate from another portion of an integrated process.

As the rotary drum completes its rotation into discharge zone 324e, the wet filter cake is removed from the compartments 332 by steam into material passageway 320e designated as a product chute (here, providing aromatic carboxylic acid-rich stream 197). In certain embodiments, steam may be introduced into the plenum 318 through inlet 321. The person of ordinary skill in the art will appreciate that, in such embodiments, the steam may disturb the cake on the filter members 334 sufficiently to remove the wet filter cake from the surface of the filter member. In other embodiments, control head 316 may be configured to deliver steam to plenum 318 through the corresponding outlet pipes 336 of compartments 332 while located in discharge zone 324e. The person of ordinary skill in the art will appreciate that, in such embodiments, the steam passes through the filter member 334 towards the filter cake, providing a pressure differential reversed relative to that of zones 324a-324d sufficient to remove the wet filter cake from the surface of the filter member. In certain embodiments using steam, removal of the wet filter cake may be further assisted by gravity.

Figure 4:
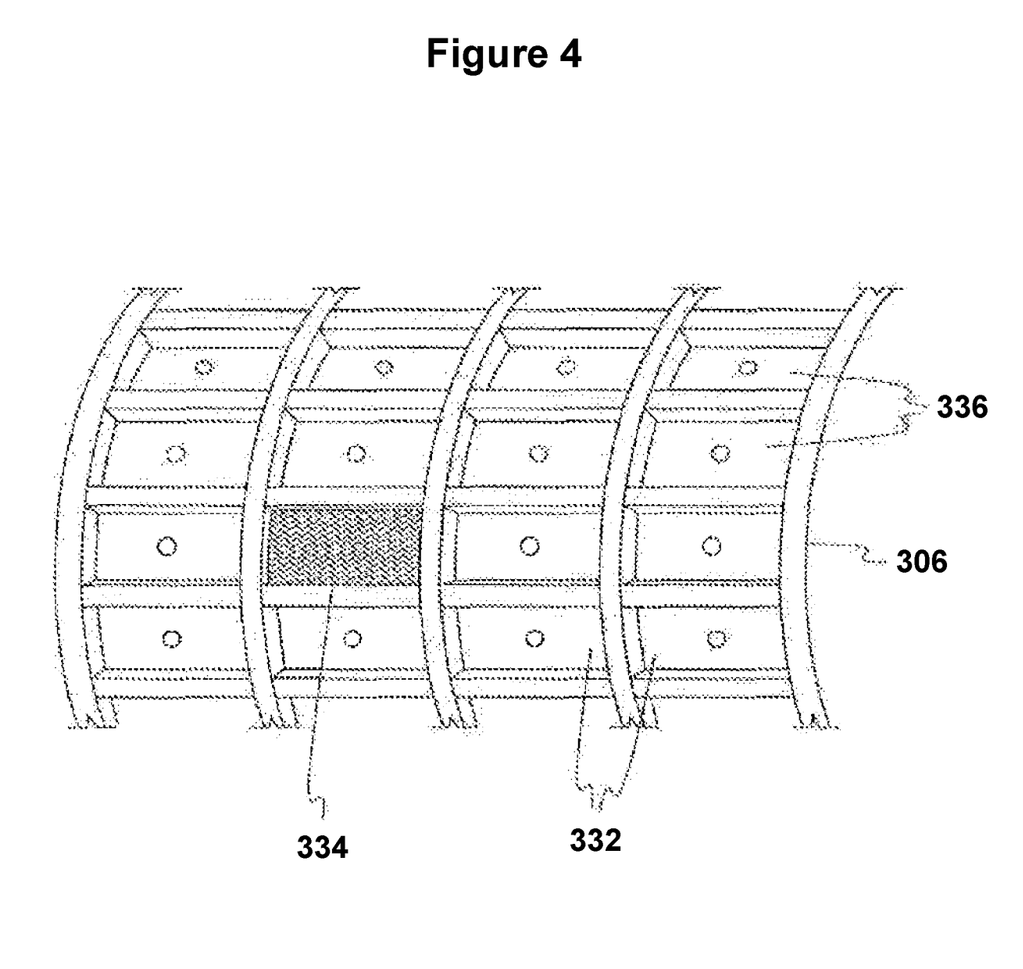
FIG. 4 shows a perspective view of a portion of a rotary drum of the rotary pressure filter apparatus shown in FIGS. 2-3.

In the embodiment shown in FIGS. 2-4, the rotary pressure filter apparatus 300 includes a single feed zone 324a, three wash zones 324b, 324c, 324d, and a single discharge zone 324e. In other embodiments of the invention, the rotary pressure filter apparatus could have one or two wash zones, or more than three wash zones, and/or one or more dry zones.

In certain embodiments as otherwise described herein, at least a portion of the wet filter cake removed from separation device 190 (here, rotary pressure filter apparatus 300) is provided as aromatic carboxylic acid-rich stream 197. As shown in FIG. 1, the aromatic carboxylic acid-rich stream 197 from the separation device 190 comprising crude solid product may be directed to a mixing zone including a reaction mixture make up vessel 200. The crude solid product in stream 197 may be mixed and slurried in make-up vessel 200 with a make-up solvent entering vessel 200 through line 202 to form a purification reaction mixture comprising crude aromatic carboxylic acid. The purification reaction mixture prepared in vessel 200 is withdrawn through line 204. In some embodiments, the purification make-up solvent contains water. In some embodiments, the solvent line 202 connects to a holding vessel (not shown) for containing make-up solvent. In other embodiments, the solvent comprises demineralized water. In other embodiments, the solvent is supplied from another part of the integrated process 100. For example, in one embodiment, the solvent comprises liquid-phase component 182 of off-gas treatment zone 180. In another embodiment, the solvent comprises the liquid-phase stream 234 exiting solid/liquid separator 230. Sources of purification make-up solvent are more fully described, for example, in U.S. Pat. Nos. 5,723,656, 6,137,001, 7,935,844, 7,935,845, and 8,173,834.

In certain embodiments as otherwise described herein, at least a portion of the aromatic carboxylic acid-rich stream is purified in a purification zone comprising a hydrogenation catalyst under reaction conditions suitable to form a purification effluent comprising purified aromatic carboxylic acid. For example, in the process depicted in FIG. 1, purification reaction mixture exiting vessel 200 through stream 204 enters purification reactor 210 of the purification zone. The purification zone may further include a pump and one or more heat exchangers (not shown) configured to pre-heat the purification mixture exiting vessel 200 before it enters purification reactor 210. In some embodiments, the purification reactor 210 is a hydrogenation reactor and purification in the purification reactor 210 comprises contacting the purification reaction mixture comprising crude aromatic carboxylic acid with hydrogen in the presence of a hydrogenation catalyst. In some embodiments, at least a portion of a purification effluent comprising purified aromatic carboxylic acid may be continuously removed from hydrogenation reactor 210 in stream 211 and directed to a crystallization zone 220 downstream of the purification zone. Crystallization zone 220 may comprise a plurality of crystallizers. In some embodiments, in crystallization zone 220, purified aromatic carboxylic acid and reduced levels of impurities may be crystallized from the reaction mixture. The resulting solid/liquid mixture comprising purified carboxylic acid solids formed in crystallization zone 220 may be fed, in stream 221, to a solid/liquid separation device 230, configured to separate the solid/liquid mixture into a liquid-phase stream 234 and an aromatic carboxylic acid-rich stream 236 comprising solid purified aromatic carboxylic acid.

As noted above, solid/liquid separation device 230 can be a rotary pressure filter such as, for example, rotary pressure filter apparatus 300 as otherwise described herein and as depicted in FIGS. 2-4.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for recovering a solid aromatic carboxylic acid from a solid/liquid mixture of the solid aromatic carboxylic acid in a solvent, the solid aromatic carboxylic acid comprising terephthalic acid or isophthalic acid and being in the form of a collection of particles having a distribution of particle sizes having a median particle size, the method comprising:
    filtering the solid/liquid mixture to form a filter cake on a filter surface, the filter cake comprising the solid aromatic carboxylic acid; and
    removing the filter cake from the filter surface;
    wherein the average pore size of the filter surface is greater than the median particle size of the collection of particles, and further wherein the median particle size of the collection of particles is at least 50% and less than 95% of the average pore size of the filter surface; and the median particle size of the collection of particles is within the range of 80 µm to 200 µm.

2. The process of claim 1, wherein the median particle size of the collection of particles is less than 90% of the average pore size of the filter surface.

3. The process of claim 1, wherein the median particle size of the collection of particles is at least 60% of the average pore size of the filter surface.

4. The process of claim 1, wherein the median particle size of the collection of particles is within the range of 100 µm to 180 µm.

5. The process of claim 1, wherein the solvent comprises a monocarboxylic acid solvent.

6. The process of claim 5, wherein filtering the solid/liquid mixture takes place using a rotary pressure filter, and the solid/liquid mixture is transferred to the rotary pressure filter from a crystallization zone in which the aromatic carboxylic acid is crystallized.

7. The process of claim 1, wherein the solvent comprises water.

8. The process of claim 7, wherein filtering the solid/liquid mixture takes place using a rotary pressure filter, and the solid/liquid mixture is transferred to the rotary pressure filter from a purification zone in which the aromatic carboxylic acid is purified.

9. The process of claim 1, further comprising washing the filter cake to form a wet filter cake.

10. The process of claim 9, further comprising drying the wet filter cake before removing the filter cake from the filter surface.

11. The process of claim 9, further comprising removing a wet filter cake from the filter surface without substantially drying the filter cake, and transferring at least a portion of the removed wet filter cake to a mixing zone, the mixing zone configured to mix and slurry the wet filter cake with a make-up solvent to provide a purification reaction mixture comprising solid aromatic carboxylic acid.

12. The process of claim 11, further comprising transferring at least a portion of the purification reaction mixture to a purification zone, the purification zone comprising a hydrogenation catalyst under reaction conditions suitable to form a purification effluent comprising purified aromatic carboxylic acid.

13. The process of claim 1, wherein the monocarboxylic acid solvent comprises acetic acid.

14. The process of claim 1, wherein the median particle size of the collection of particles is at least 50% and less than 85% of the average pore size of the filter surface.

15. The process of claim 1, wherein the median particle size of the collection of particles is at least 60% and less than 95% of the average pore size of the filter surface.

16. The process of claim 1, wherein the median particle size of the collection of particles is at least 60% and less than 85% of the average pore size of the filter surface.

17. The process of claim 1, wherein the median particle size of the collection of particles is at least 60% and less than 85% of the average pore size of the filter surface; and the median particle size of the collection of particles is within the range of 100 µm to 180 µm.

* * * * *